(12) United States Patent
Murdock et al.

(10) Patent No.: US 10,737,165 B2
(45) Date of Patent: Aug. 11, 2020

(54) SMART SYSTEM FOR DISPLAY OF DYNAMIC MOVEMENT PARAMETERS IN SPORT AND TRAINING

(71) Applicants: Wilbert Quincy Murdock, Bronx, NY (US); Philip Alister Williams, Salt Point, NY (US)

(72) Inventors: Wilbert Quincy Murdock, Bronx, NY (US); Philip Alister Williams, Salt Point, NY (US)

( * ) Notice: Subject to any disclaimer, the term of this patent is extended or adjusted under 35 U.S.C. 154(b) by 0 days.

(21) Appl. No.: 15/842,878

(22) Filed: Dec. 15, 2017

(65) Prior Publication Data

US 2018/0117438 A1 May 3, 2018

Related U.S. Application Data

(60) Continuation of application No. 12/799,520, filed on Apr. 26, 2010, which is a division of application No.
(Continued)

(51) Int. Cl.
*A63B 69/36* (2006.01)
*A63B 24/00* (2006.01)
(Continued)

(52) U.S. Cl.
CPC .......... *A63B 69/36* (2013.01); *A63B 24/0006* (2013.01); *A63B 24/0021* (2013.01);
(Continued)

(58) Field of Classification Search
CPC ..... G01S 19/26; A63B 69/36; A63B 69/3614; A63B 24/0006; A63B 24/0021; A63B 24/0084; A63B 67/02
(Continued)

(56) References Cited

U.S. PATENT DOCUMENTS 3,792,863 A * 2/1974 Evans ................ A63B 69/3632
340/669
5,056,791 A * 10/1991 Poillon .............. A63B 24/0021
473/156
(Continued)

*Primary Examiner* — Allen Chan
(74) *Attorney, Agent, or Firm* — Robert DeWitty; DeWitty and Associates, Chtd.

(57) ABSTRACT

A system that wirelessly integrates actual golf equipment, game apparatus, or gaming tool, with a computer and the internet to allow players remotely located from one another to play a competitive real or simulated game. An individual player may opt to play solo or practice to improve basic golfing or sports techniques. The system includes any sports implement or smart golf clubs, a golf ball receptacle and a golf club motion sensing devices, all containing circuits and contact and or noncontact motion sensors coupled with signal processing and radio frequency transmitter circuitry to wirelessly communicate game performance information to a remote receiver-computer. The computer display screen displays player information and visually simulates and controls a game between one or more local computer players or via the internet having similar equipment and remotely located from each other. The computer displays player information such as anatomical motion or data, game apparatus, gaming tool, or sports implement information simultaneously, and visually simulates and controls a game between two players via the internet having sports equipment remotely located from each other, providing graphics animation and graphics to learn and compete by. Standard sports implements may be retrofitted with the sensors and associated circuitry to convert such implements as clubs into "smart dubs" for use with the system. The system employs specially developed computer software to process player performance data, control game play, communicate game information between players, generate and control visual simulations and display player performance information and dynamic motion parameters.

13 Claims, 14 Drawing Sheets

Related U.S. Application Data

09/570,233, filed on May 12, 2000, now Pat. No. 7,789,742.

(60) Provisional application No. 60/133,722, filed on May 12, 1999.

(51) Int. Cl.
*A63B 67/02* (2006.01)
*G01S 19/26* (2010.01)
*A63B 63/00* (2006.01)
*A63B 71/06* (2006.01)
*A63B 57/40* (2015.01)
*A63B 57/30* (2015.01)
*A63F 9/24* (2006.01)

(52) U.S. Cl.
CPC .......... *A63B 24/0084* (2013.01); *A63B 67/02* (2013.01); *A63B 69/3614* (2013.01); *G01S 19/26* (2013.01); *A63B 24/0062* (2013.01); *A63B 24/0075* (2013.01); *A63B 57/357* (2015.10); *A63B 57/40* (2015.10); *A63B 63/00* (2013.01); *A63B 69/3632* (2013.01); *A63B 69/3655* (2013.01); *A63B 69/3658* (2013.01); *A63B 69/3676* (2013.01); *A63B 69/3685* (2013.01); *A63B 69/3688* (2013.01); *A63B 71/0616* (2013.01); *A63B 71/0622* (2013.01); *A63B 71/0669* (2013.01); *A63B 71/0686* (2013.01); *A63B 2024/0034* (2013.01); *A63B 2024/0037* (2013.01); *A63B 2024/0056* (2013.01); *A63B 2024/0068* (2013.01); *A63B 2071/063* (2013.01); *A63B 2071/065* (2013.01); *A63B 2071/0647* (2013.01); *A63B 2220/00* (2013.01); *A63B 2220/13* (2013.01); *A63B 2220/16* (2013.01); *A63B 2220/30* (2013.01); *A63B 2220/62* (2013.01); *A63B 2220/801* (2013.01); *A63B 2220/833* (2013.01); *A63B 2220/89* (2013.01); *A63B 2225/20* (2013.01); *A63B 2225/50* (2013.01); *A63F 9/24* (2013.01)

(58) Field of Classification Search
USPC ................................................ 463/3; 473/155
See application file for complete search history.

(56) References Cited

U.S. PATENT DOCUMENTS

| | | | | |
|---|---|---|---|---|
| 5,221,082 A | * | 6/1993 | Curshod | A63B 24/0021 434/252 |
| 5,390,927 A | * | 2/1995 | Angelos | A63B 24/0021 434/252 |
| 5,437,457 A | * | 8/1995 | Curchod | A63B 24/0021 434/252 |
| 5,846,139 A | * | 12/1998 | Bair | A63B 24/0021 473/156 |
| 5,906,547 A | * | 5/1999 | Tynan | A63B 24/0003 473/199 |
| 5,949,679 A | * | 9/1999 | Born | A63B 71/0669 463/42 |

* cited by examiner

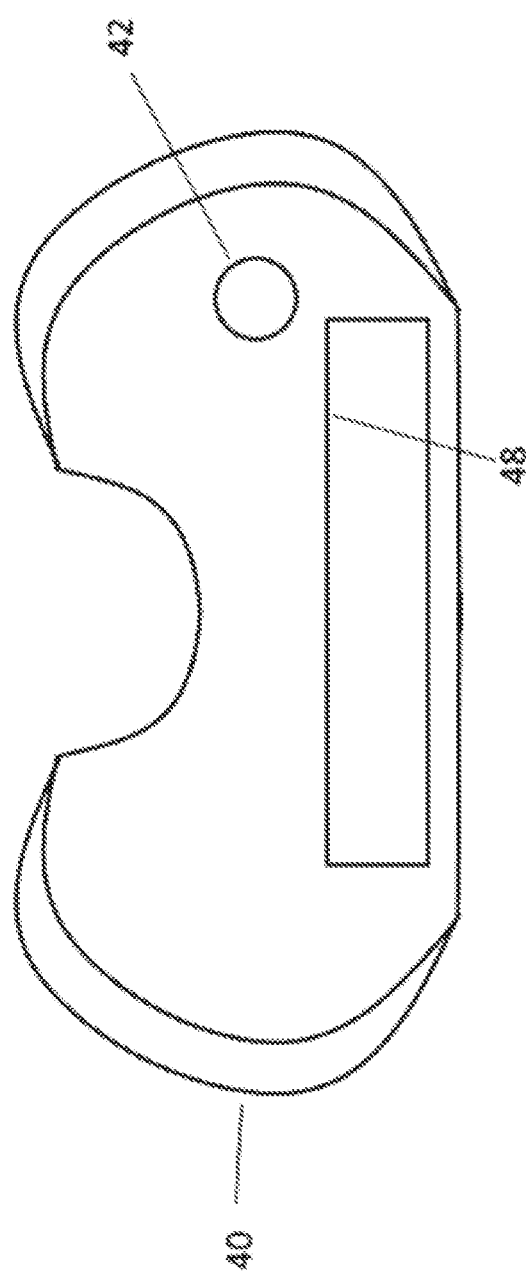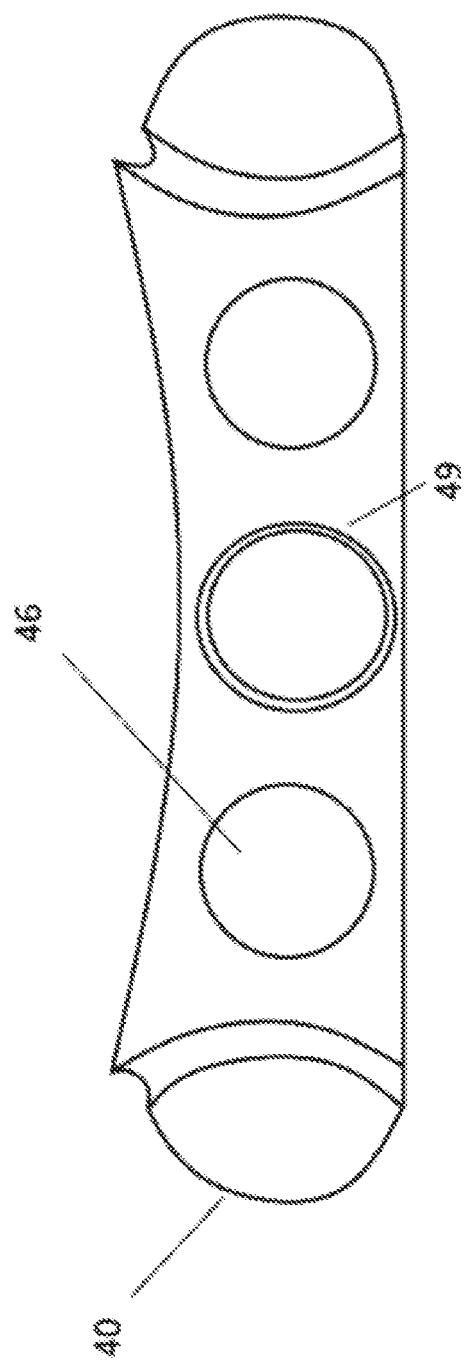

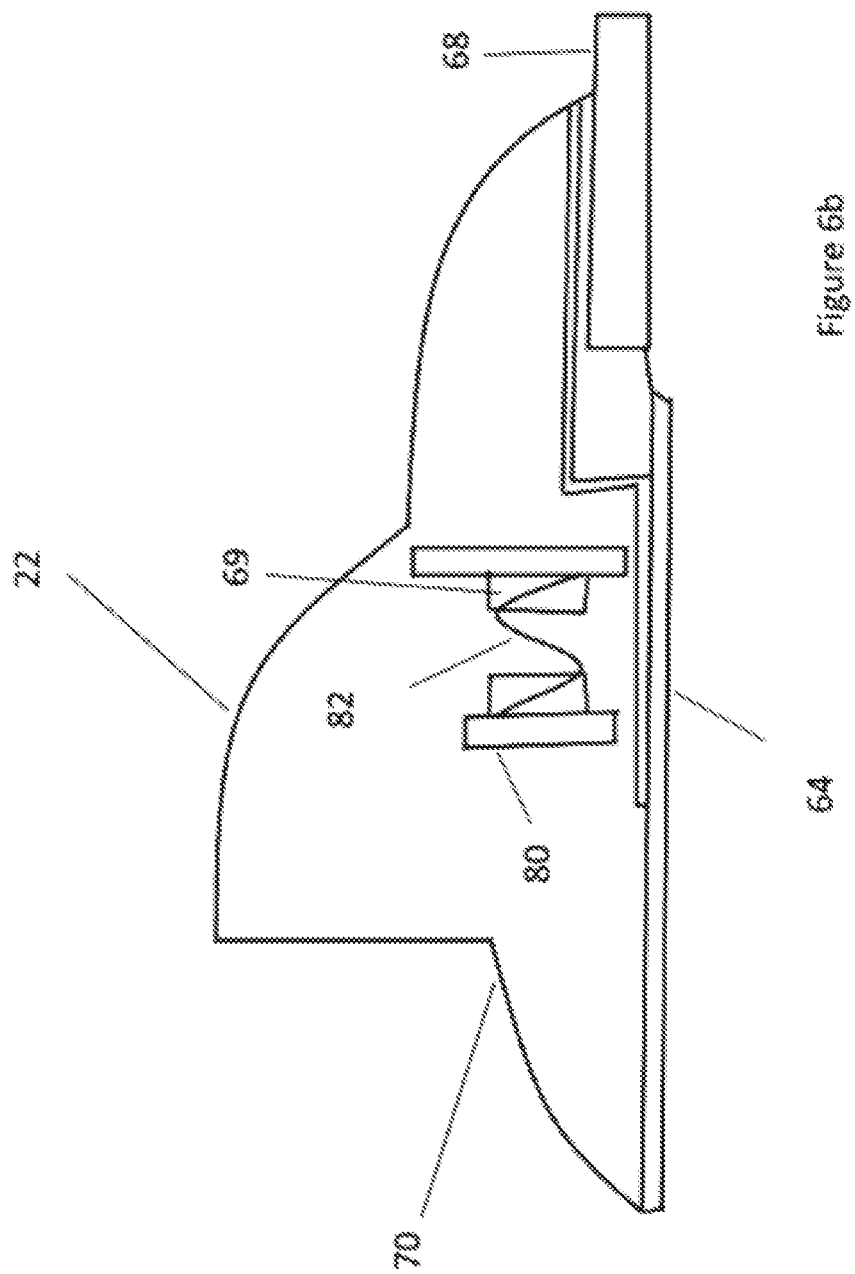

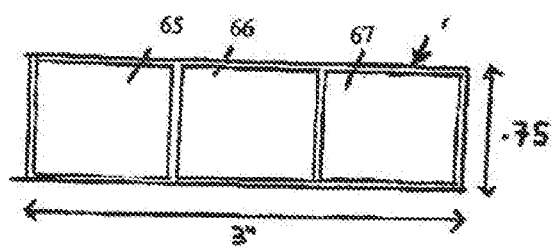
Tripad Sensor with three different activation areas
FIGURE: 7

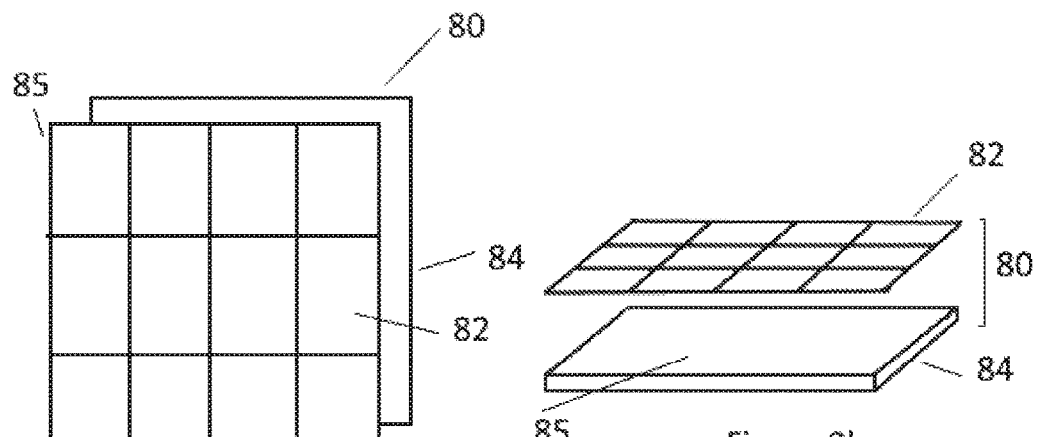
Figure 9a
Figure 9b
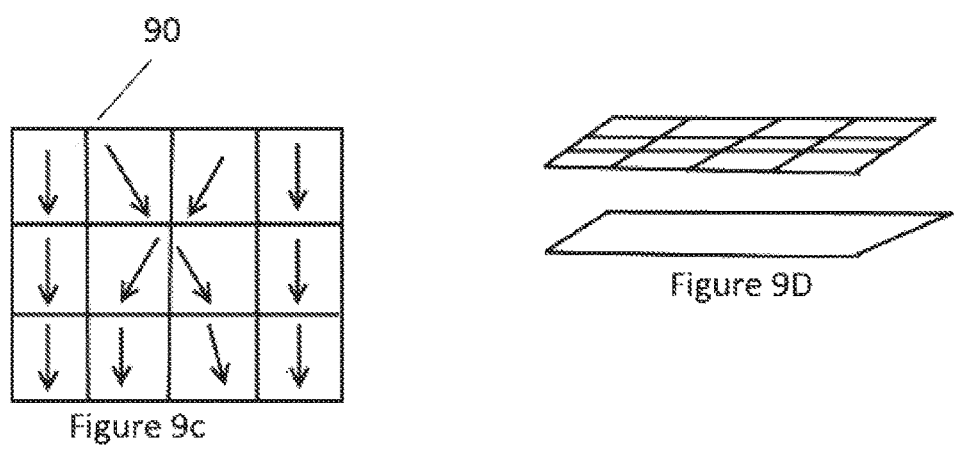
Figure 9c
Figure 9D
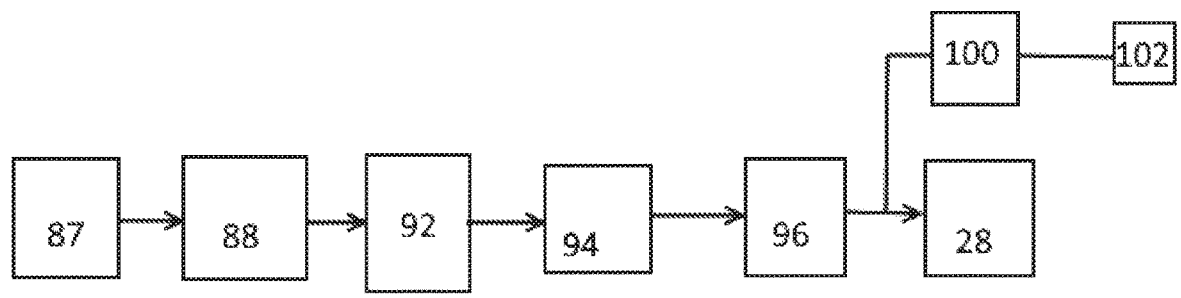
Figure 9E Visual Gaming Software Process Flow Diagram

SMART SYSTEM FOR DISPLAY OF DYNAMIC MOVEMENT PARAMETERS IN SPORT AND TRAINING

PRIORITY CLAIM

This application is a continuation of U.S. patent application Ser. No. 12/799,520, filed Apr. 26, 2010, which is a divisional and claims the benefit and priority of application of Ser. No. 09/570,233, filed May 12, 2000, which, in turn, claims the benefit and priority of U.S. provisional application Ser. No. 60/133,722, filed May 12, 1999. The referenced applications are incorporated herein by reference as if restated in full.

FIELD OF INVENTION

This invention relates to sports implements such as a smart golf system coupling real sports equipment and a computer. More particularly, this invention relates to a system wherein a sports implement such as a golf club, hockey stick, baseball bat, tennis racket, boxing gloves, soccer ball, volleyball, baseball, football, bowling ball, hockey puck, race car steering wheel, or other game apparatus communicates dynamic contact and movement parameters wirelessly to a personal computer and thereby, if desired to the internet.

BACKGROUND OF THE INVENTION

Resolving an object's direction post impact is a problem that has been addressed in the literature often with great complexity. In addition, few high-tech solutions have been employed but may be unsuitable for use under repeated impact of the object and impact surface.

A number of patented sports implements as in the case of golf club devices embody various ball contact or club swing sensing components. Typically, these devices display information related to a golf player's swing and accuracy in hitting a golf ball. In certain of these, the information is displayed or signaled by some of the golf club itself in the form of a small visual readout or an audible sound. One such device contains an array of mechanically irrepressible pins on the face of the golf club. When the ball is struck by the club. the pins are physically depressed in a pattern to inform the player of the location on the club face where contact with the ball occurred. Another device uses a light emission and reflection detection technique to provide a player's information, displayed on the club, regarding the alignment of the golf ball with the preferred location on the golf club face.

Also, numerous conventional computer sports golf game software packages and video games use a variety of unrealistic techniques to emulate the striking of a golf ball with a club. None of these cooperates with actual golf clubs, actual golf ball target, or cup receptacles, or a swing detector that senses the actual golf stroke.

It is desirable to remotely communicate actual player performance location, whereby more sophisticated analysis and prediction possibilities are realizable via computer technology and state-of-the-art display techniques. Further, it is also desirable to use such performance information in an expanded capacity to provide interactive competitive play among numerous players in locations remote from each other.

SUMMARY OF INVENTION

This invention relates to a system that interconnects real golf or other sports equipment to a computer. In a preferred embodiment the computer is coupled wirelessly to a golf club, a receptacle or a swing sensing component. From hereon, sports apparatus, sports equipment, sports equipment items, are examples of a gaming apparatus, unit, tool, or item, and the latter should be understood to be included in the former. In a preferred embodiment the computer is coupled wirelessly to a sports implement component. In one embodiment, the sporting equipment is a hockey stick, coupled with a hockey puck, race car steering wheel coupled with a driver's hand, bow coupled with an arrow, boxing gloves coupled with a fist, tennis racket, coupled with a tennis ball, basketball ball coupled with a shooting hand, football coupled with a throw, bicycle coupled with a pedal, bowling ball coupled with a bowling throw, soccer coupled with a kick, volleyball coupled with a hitting hand, baseball bat coupled with a baseball, all using sensors including accelerometers, gyroscopes and a compass and or a combination of multiple sensing devices: It should be noted that sports like football would require a sensor based football and sensors on the hand of the quarterback for a full range of interactive data. Further, the invention, with components summarized below, allows one or more golfers to enter into a golf competition against each other. Each player asks the computer who is available to play a contest. Once a player's pairs up against another player anywhere in the world and play ensues, the computer display screens show each participant's score via animation or graphics that preferably relate to a player's individual performance statistics. A single player may play without an opponent to practice and improve basic sports or golfing skills using the computer and display to track performance.

The system application is unlimited. Much of this system can be used not only for golfing competition on the Internet, but for other sports as well. Sports implements other than golf clubs, swing detectors and receptacles can be outfitted with sensors according to this invention and used for training purposes, rehab, or for interactive internet game competition.

The system technology can also be used for training, competition, and the improvement of player reflexes and coordination, with little or no modification. The technology also has applications in medicine, particularly physical therapy.

Smart Golf Club

A wireless golf club is constructed to contain, or alternatively, a standard golf club is modified to contain, a multiple sensor or transducer array located on the club head at the face or hitting surface. A wireless piece of sporting equipment is constructed to contain, or alternatively a standard piece of sporting equipment is modified to contain, a multiple sensor or transducer array located on the surface of said sports equipment, gaming apparatus, gaming tool or sports implement and GPS sensing circuitry and gyroscope. Upon impact of the head of the club with a golf ball, the impacted sensors produce detectable variances representing the magnitude and duration of the club-ball impact force and impulse and the proximate location of such contact relative to the preferred location, the "sweet spot", on the face of the club head. The variances are electronically processed into digitally coded information and remotely transmitted by an electrical communication circuit either contained within or attached to the golf club.

In each golf club device and golf ball receptacle device according to this invention. in a preferred embodiment the transducers are or include piezoactive elements and or pressure sensors. As used herein. "piezoactive" includes piezoelectric and piezoresistive components. Piezoactive components are defined as components with the electrical properties of which, when the component is subjected to physical force, vary.

The smart golf club system uses biofeedback to create an intelligent golf training and entertainment system, ergo a smart golf club. The smart golf club system is a diagnostic and analysis tool used to improve a player's skills by relatively instantaneous visual cues and acoustic feedback with little or no human intervention. The smart golf club system takes the generated data and reconstructs it into a useful visual format that can be presented in a variety of ways including 3-dimensional animation.

The smart golf club system integrated circuit or circuits can be located anywhere within the club including the head and or shaft. The smart golf club has a means via its built-in microcontroller to process, analyze, store, hitting pattern data and transmit it to the computer and or the Internet for further analysis. In playback mode the smart golf club system memorizes how many times each sensor was hit. This provides the golfer information about his or her hitting pattern. Using a computer algorithm, we can analyze and calculate a hitting pattern and resulting in a personalized sports hitting detection system for each athlete.

A self-recording golf club and receptacle system comprising: a. a golf club-head or shaft having an inner core surrounded by an outer cover; b. the golf club having a computer processor pre-programmed with identification information corresponding to the club, a power source, a receive and transmit device, and piezo sensors electrically connected and located on the face of the golf club-head; c. the processor is further pre-programmed (i) to record data corresponding to one stroke upon activation of the processor by the piezo sensor, (ii) to record a magnitude of force of one stroke, and (iii) to subsequently ignore signals transmitted by the piezo sensor after one stroke is received by the ball for a period of time correlative to the magnitude offeree of one stroke; d. the processor is programmed to record subsequent stroke data upon activation by the piezo sensor until later activated to erase said subsequent stroke data, and e. a golf ball receptacle for receiving the golf ball when the golf ball is struck, the receptacle having a processor, a power source, a receive and transmit device, and a piezo sensor electrically connected to one another and mounted on or within the receptacle, such that when the ball strikes the receptacle piezo sensor upon entering the receptacle, the receptacle sensor activates the receptacle processor, the receptacle processor is programmed to receive data from the golf club processor and subsequently transmit the data to a remote computer for display or storage therein. The golf club processor is further programmed such that upon transmission of data to said first computer, the data correlating to the direction, of the club face position, and magnitude of force of the strokes impacted by the ball is erased from the receptacle processor. The golf club processor is programmed to remain in a low power sleep mode prior to activation of said golf club piezo-sensor. The golf club processor and target receptacle is rechargeable and is pre-programmed with object identification data including, but is not limited to a golf ball. The golf club or sports apparatus, sports device, game apparatus, or gaming tool receive and transmit device is selected from radio frequency coils, ultrasonic devices, audio devices, vibratory devices, and optical devices.

Golf Ball Receptacle

The A ball receptacle has an open end to receive a golf ball and contains a transducer located so as to sense the ball entering the receptacle. Upon impact with the golf ball, the sensor produces a detectable variance representing impact with the ball. The variance is electronically processed into display coded information and remotely transmitted by an electrical communication circuit.

In one preferred embodiment the communication circuit is contained within the receptacle.

Preferably the communication circuit for the receptacle is a radio frequency transmitter. The receptacle can either be designed for indoor use or can be a cup in an actual green with the communication circuit housed in the cup or elsewhere conveniently located.

Golf Club Motion Sensor Plate

A golf club swing motion sensing device contains an array of uniformly distributed sensing transducers upon or proximate to the device surface. This motion sensing device may be formed as a mat or a plate or other substantially flat surface from which a golf ball is hit. The transducers produce detectable varying characteristics such as capacitance representing the velocity, angle, and proximity of a golf club relative to the surface of the device. The variances are electronically processed into digitally coded information and remotely transmitted by an electrical communication circuit contained within or electronically connected to the device.

Wireless Signal Receiver and Computer

At each remote player site, wireless radio frequency equipment receives the digitally coded transmitted signals from the golf club, the golf ball receptacle, and the club swing motion sensing device. The signals are demodulated and processed into serial binary data suitable for communications to the computer via either serial or parallel ports. As the game progresses, the computer under the control of the golfing software, monitors and directs the flow of communications between the players via the internet and displays the game simulations and performance information. Moreover, a processor or equivalently a computer processor is hereon and heretofore understood to be a microprocessor or microcomputer and each of the latter is understood to be included in the former.

Computer Golfing Software System

At each remote player site, a computer under the control of the golfing software, monitors and controls the sequential play of the game and interacts with the player at the site and also competing players at the other remote sites via the internet. The software system generates the game simulations for display and tracks each player's performance as the game progresses.

The above with further features and advantages of the invention will be better understood with reference to the accompanying drawings and the following detailed description of preferred embodiment.

BRIEF DESCRIPTION OF THE DRAWINGS

FIG. 2 is a top plan view of a golf club with sensors and circuitry and used in the computer implemented system of FIG. 1.

FIG. 3 is a front elevation view of the golf club head of FIG. 2, and shows three sensors located at the face of the club head.

FIG. 6B is a cross-sectional view along the lines B-B of FIG. 6A.

FIG. 7 is a top plan view of a golf ball sensing element with three distinct activation areas for use in the receptacle of FIGS. 6A-6C.

FIGS. 9A-9D are diagrammatic illustrations of a golf club motion or swing sensor plate for use with the system according to FIG. 1.

FIG. 9E is a block diagram of electronics used in association with the swing sensor plate of FIGS. 9A-9D.

DETAILED DESCRIPTION OF PREFERRED EMBODIMENT

Smart Golf Club

Figure 1:
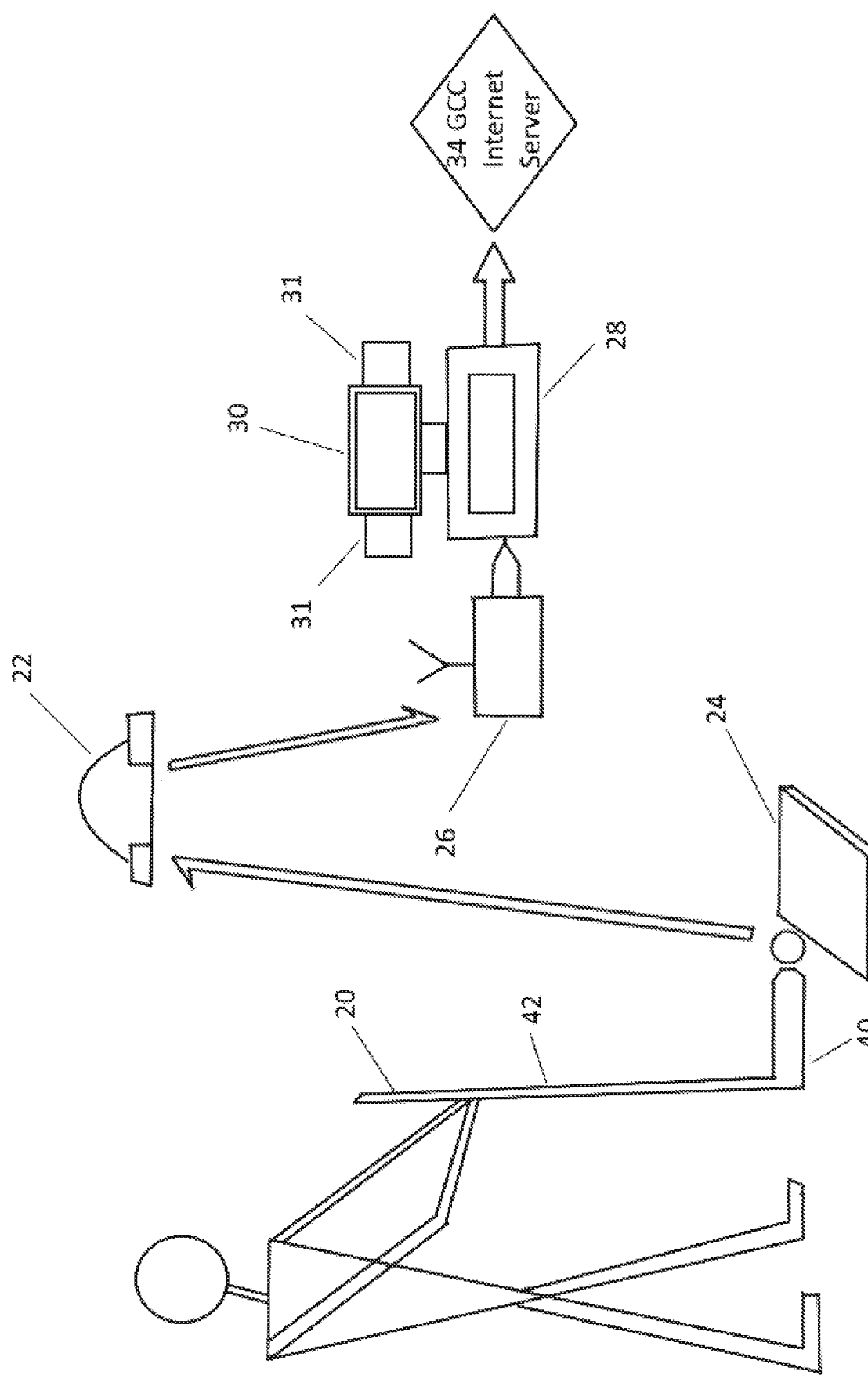
FIG. 1 is a diagrammatic illustration of components of a computer implemented golf system according to this invention.

The smart golf club 20 has a head 40 and a shaft 42. As shown in FIGS. 2 and 3, the head 40 has a shaft opening 42, a plurality of embedded contact sensors 46 (three are illustrated in the preferred embodiment), and internal electronics circuitry 48 including a wireless radio frequency transmitter (58 in FIG. 5). As shown, at least one of the sensors 46 is located at or proximate to the optimal location on a club face 47 for contact with the golf ball "sweet spot" 49. The remaining two sensors are adjacent and on either side of the sweet spot 49. The contact sensors may be, but are not limited to sensors employing piezoactive type transducers, specifically, either piezo-electric or piezo-resistive transducers (similar, but is not limited to the Cooper Instruments LPM 562).

Figure 3A:
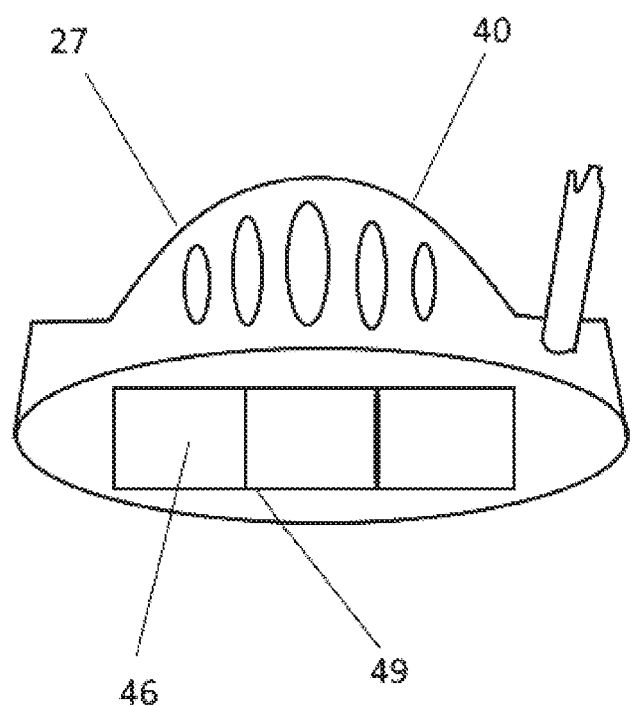
FIG. 3A is a front plan view of a further embodiment of a club head for use with the computer implemented golf system of FIG. 1.
Figure 4:
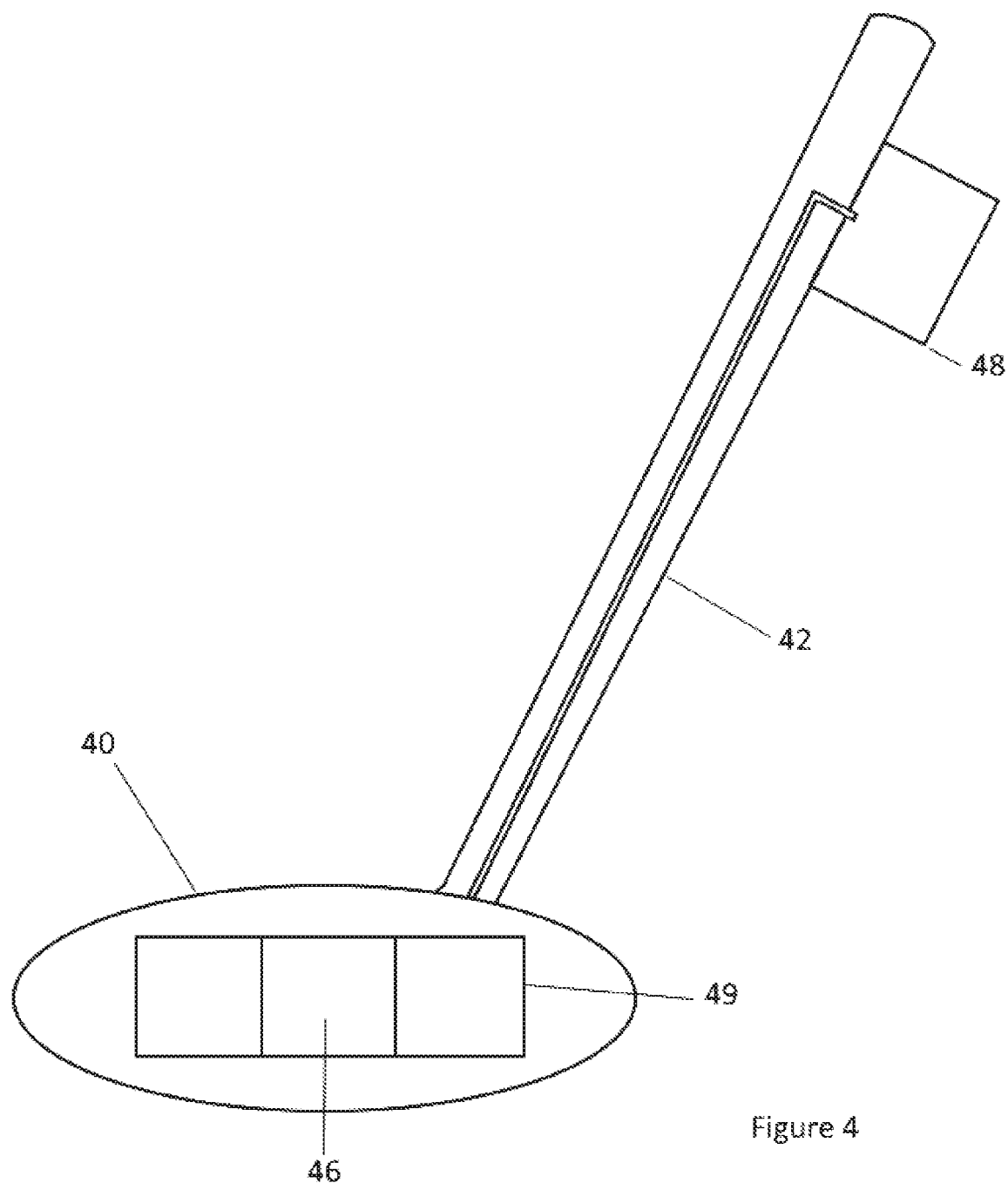
FIG. 4 is a diagrammatic front plan view of a putter with a club head and circuitry forming a further, alternative embodiment of a club for use with the computer implemented system of FIG. 1.

In an alternative embodiment. FIG. 3A, three sensors 46 are applied to the face of an adapted club by a Mylar tape or other means 49. Again, the electronic circuitry is internal to the club head 40 and connects to the sensors 46 by leads 27. In a second alternative embodiment, to retrofit a standard golf club, contact sensors 46 are part of an adapter 40 attached to an ordinary club head as seen in FIG. 4 and wire connected to an electronic circuitry 48, attached to the club shaft 42 or elsewhere on the club.

Figure 5:
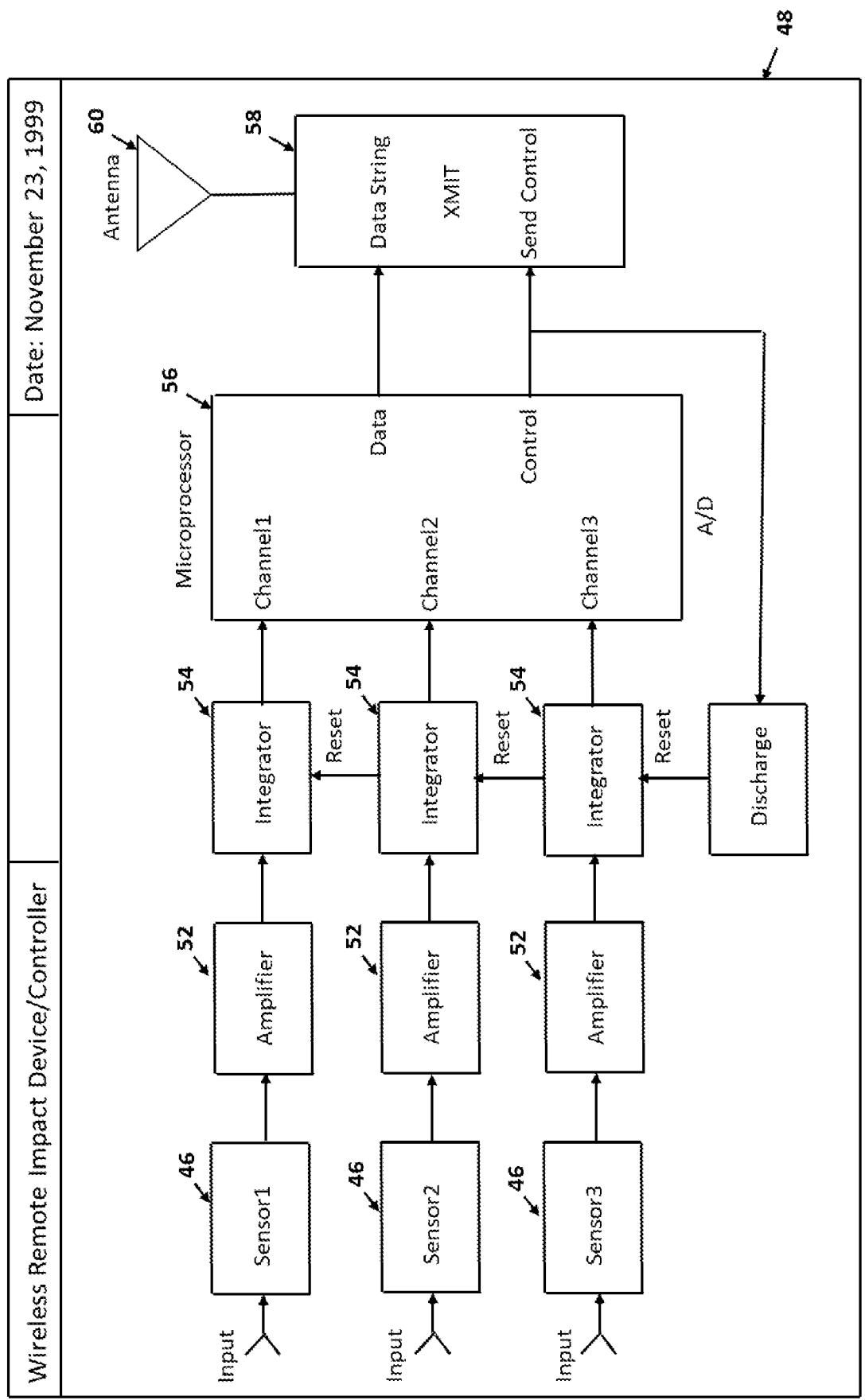
FIG. 5 is a schematic block diagram of a club head electronics installation for use with the club heads of FIGS. 2-4.

A golf ball contacting any sensor 46 produces a detectable variance indicating the magnitude and duration of sensor-ball impact (impulse). The variance may be a change in resistance of a piezo-resistive transducer or a voltage change in the case of a piezo-electric transducer. As shown in FIG. 5, the variance is detected and amplified by an associated amplifier 52 and is the input to an associated integration circuit 54, the output of which represents the energy of the ball-club contact event.

Connected to the integration circuit 54, a processor 56 is a multi-input signal processing circuit (similar, but not limited to a Motorola #68HCOS) having analog to digital signal converting circuits (ADCs), one for each input channel, and a sequential digital signal encoding circuit connected so as to convert the ADC outputs into a time multiplexed serial digital data stream containing a binary-coded word for each channel indicating the energy of the associated sensor-ball impact event.

A radio frequency transmitting circuit 58 receives the serial digital data from the processor 56 and wirelessly transmits the information via an internal antenna 60 to a receiver 26 (FIG. 1) for subsequent processing by the computer 28.

Golf Ball Receptacle

Figure 6A:
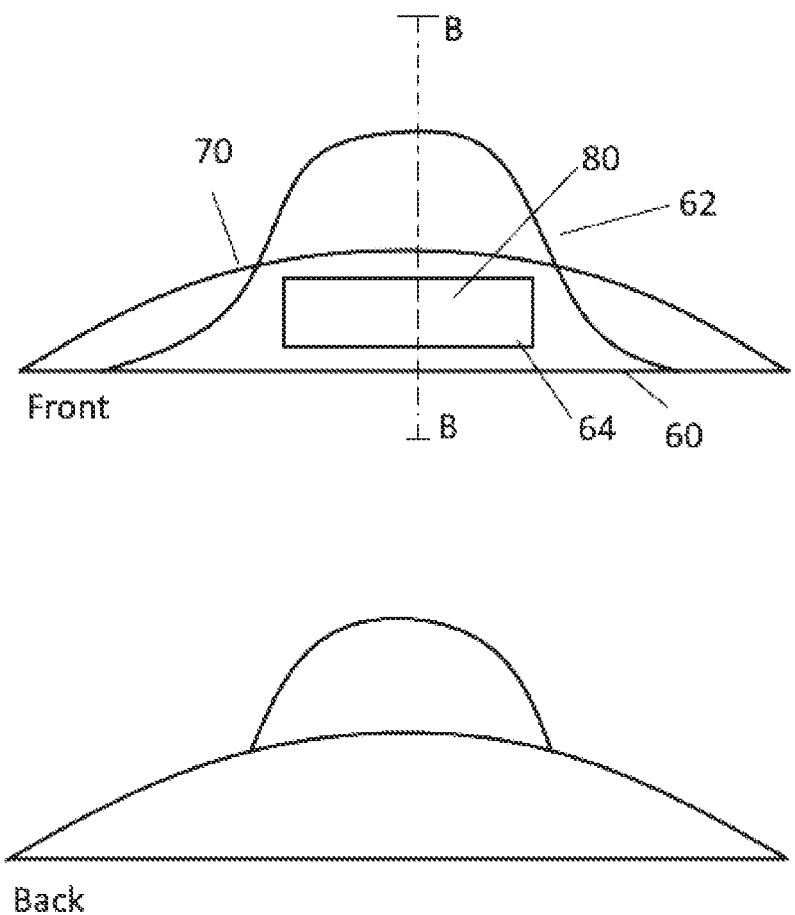
FIG. 6A is a front elevation view of a golf ball receptacle for use with the system of FIG. 1.
Figure 6C:
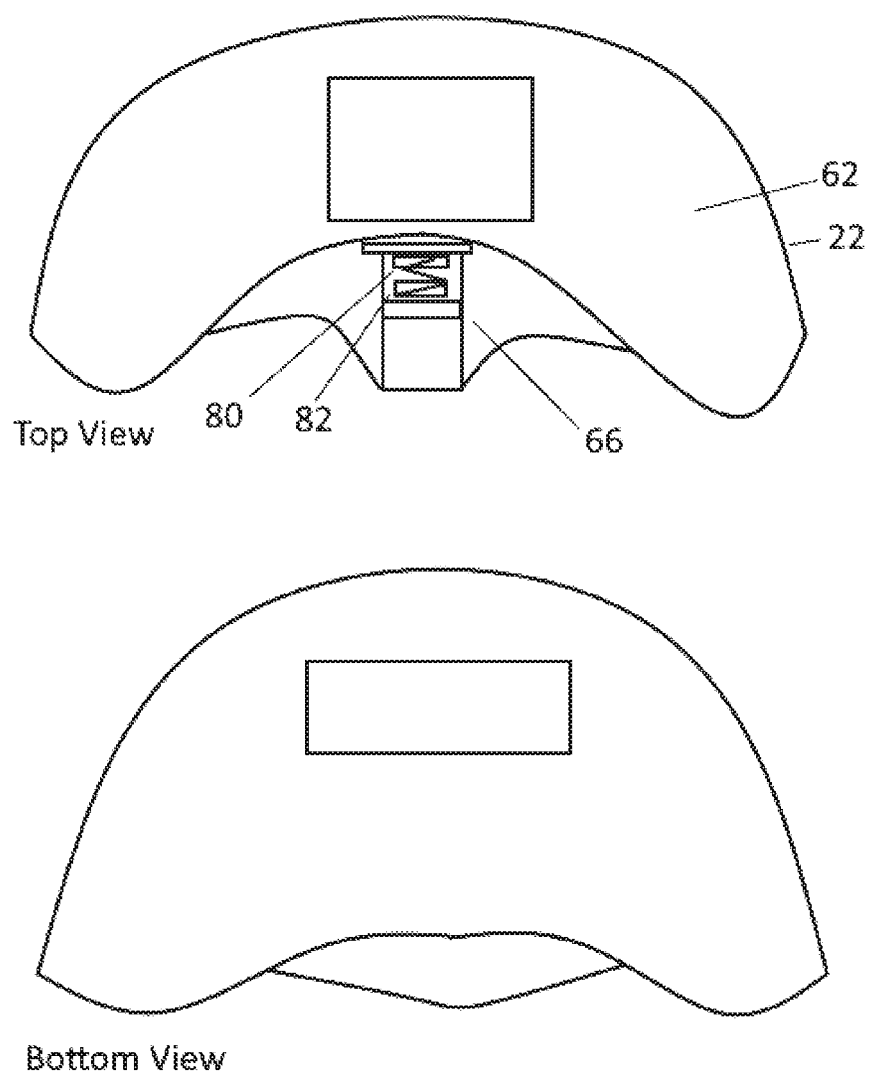
FIG. 6C is a fragmentary top plan view of the receptacle of FIGS. 6A and 6B illustrating internal components of the receptacle.

The golf ball receptacle 22 has a top 62 shaped to allow entry of a golf ball, as shown in FIGS. 6A, 6B, and 6C. The receptacle has a contact sensor pad 64, shown in FIG. 7, containing at least one contact sensor (three different activation areas 65, 66, and 67 are illustrated in the preferred embodiment), a ball return mechanism 69 (FIG. 6B) and internal electronic circuitry 68 (FIG. 6B). The internal circuitry includes a wireless radio frequency transmitter (not separately shown in FIGS. 6A, 6B and 6C). As shown, the preferred embodiment has contact sensor pad 64 positioned within the receptacle 60 such that the center activation area 66 aligns with the center of a ball entry 70. Additional sensor activation area 65 and 67 are adjacent, one on either side of the center area 66. In the preferred embodiment, of FIGS. 6A, 6B, and 6C, and like the sensor used at the face of the club, the sensors may be, but are not limited to, sensors employing piezo active type transducers, specifically, either piezo-electric or piezo-transducers.

Figure 8:
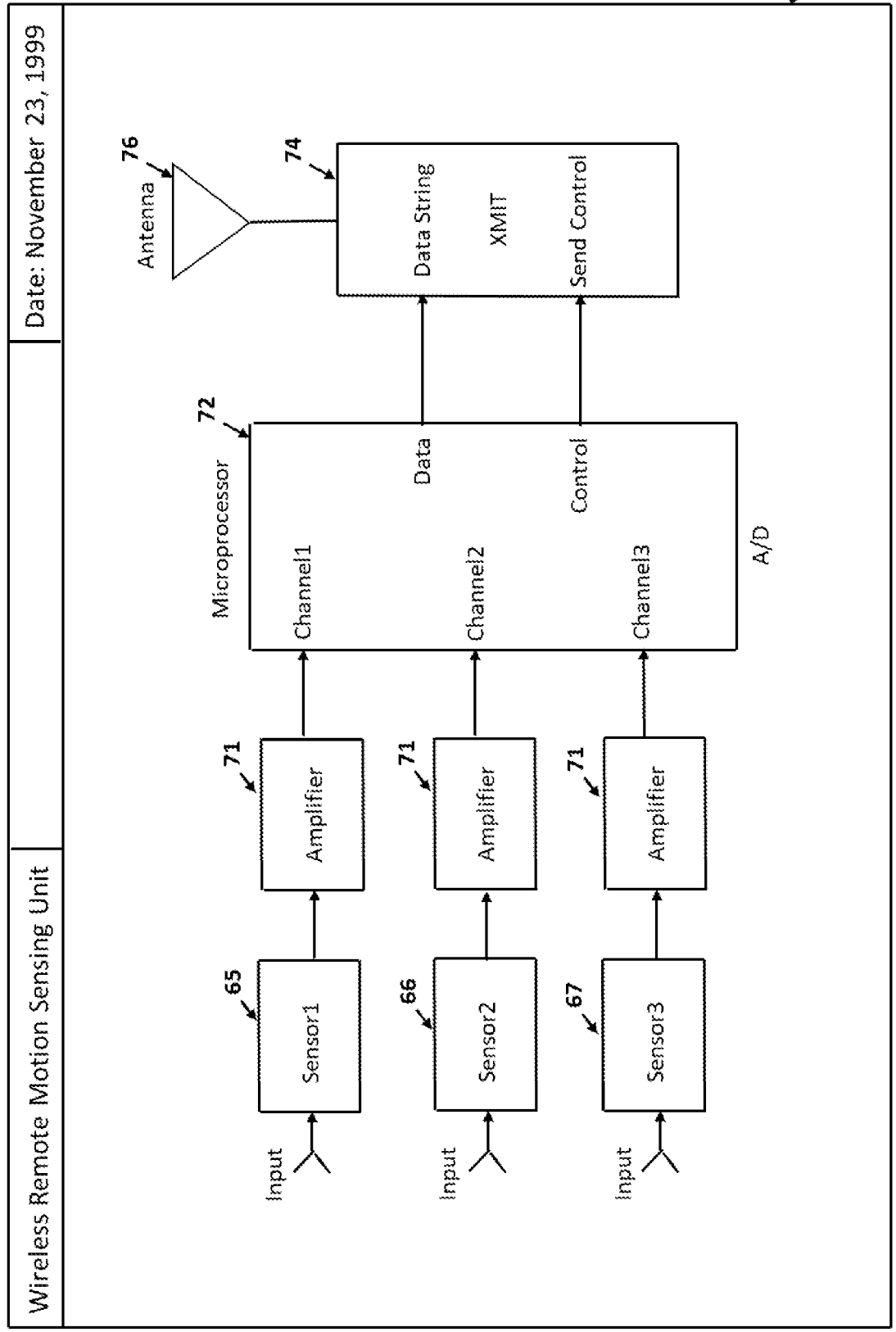
FIG. 8 is a schematic block diagram of a receptacle electronics installation for communicating with the computer in a computer implemented system according to FIG. 1.

A golf ball entering the receptacle 60 and containing the sensor pad 65, 66, or 67 produces a detectable variance indicating the ball entry event. The variance may be a change in resistance in the case of a piezo-resistive transducer (similar, but not limited to Cooper Instruments LPM 562) or a voltage change in the case of a piezo-electric transducer. As illustrated in FIG. 8, the variance is detected and amplified by an associated amplifier 71. The amplified signal then is input to a processor 72 having an analog to digital signal converting circuit (ADC) and a digital signal encoding circuit connected so as to convert the ADC output representing the sensors signals into a serial digital data stream containing a binary coded word indicating the sensor-ball contact event. The processor 72 may be the same or similar to the processor 56 of the golf club electronics. A radio frequency transmitter circuit 74 receives the serial digital data from the processor 72 and wirelessly transmits the information via an internal antenna 76 to the receiver 26 (FIG. 1) for subsequent processing by the computer 28.

The ball return mechanism 68 can be simple as a back plate 80 located to be engaged by a golf ball entering the receptacle 22 and supported and biased by a spring or springs 82 to eject the ball. Other known ejection devices, similar to those used in pinball machines and either mechanically or even electrically activated, can be used to improve the effect if desired. The receptacle configuration is susceptible to much variation. The receptacle illustrated and described above is well suited to indoor use, on carpet for example. It is clear, however, that an actual cup, installed in an actual green, with real or synthetic grass, can be similarly equipped.

Motion Sensor Plate

The golf club motion sensor plate 80 having a top motion plate 82 and a bottom motion plate 84 is diagrammatically shown in FIGS. 9A-D, wherein the top motion plate 82 contains a plurality of capacitor-forming electrically isolated platelets 83 (twelve platelets are illustrated in this exemplary preferred embodiment). They are evenly distributed at or just below the top plate's exterior upper surface 82. The bottom plate 84 has a homogenous electrically conductive interior surface 85 underlying the platelets 83. Each capacitive platelet 83 contained in the top motion plate 82 forms a capacitive component when the top and bottom motion plates are vertically closely spaced to form the golf club motion sensor plate. A suitable insulator may be sandwiched between the two plates. The structure is adhesively or otherwise mechanically joined and it may be covered or coated as desired. The result is a golf club motion sensor plate 80 containing a capacitor matrix (a 3×4 capacitor matrix) is illustrated in the preferred embodiment. The capacitive components 83 are connected to form a capacitive network 88 as is indicated in FIG. 9E.

Applying an energizing high frequency alternating electrical signal having a frequency in the range from 100 MHz to 200 MHz from an oscillator 87 to the golf club motion plate capacitive network 88 produces an electromagnetic field above the surface of each platelet 83 of the capacitive components of the motion sensor plate 80. Any object, including a golf club, passing near the surface of the energized motion plate will cause a perturbation of the electromagnetic field as illustrated by the sample possible pathways 90 across the plate in FIG. 9C. A network 92 of electrical comparator amplifiers (FIG. 9B) is connected to the capacitor network. The comparators of the network 92 are connected one to one with the capacitive elements of the capacitive network 88. The comparators of the network 88 detect voltage variations occasioned by electromagnetic field disturbance due to a golf club moving over certain of the capacitive elements of the motion plate. Each different golf club motion over the energized motion plate will produce a uniquely identifiable signal from the comparator amplifier network. There are a variety of known proximity sensors that could be gathered together in an array like that of the platelets 83 to serve as the transducer portion of the golf club motion detector.

The electrical signal from the comparative amplifier network 92 is applied to an analog to digital signal converter 94 (ADC) and the ADC digitized output signal is converted into a serial digital data stream by a multiplexer 96. This data identifies each platelet having had its field disturbed.

The serial digital data can be input directly by wire from a multiplexer 96 to the computer 28 located at the site of the golf player and golf club motion sensor plate 80, or as in the preferred embodiment, illustrated in FIG. 1, the serial data can be transmitted 100 and an antenna 102, included in the golf club motion electronic transmitter communication circuitry from FIG. 1.

The computer 28 under the control of the golf system software, will analyze the serial digital club motion signal, recognize from the transmitted signals the platelets 83 over which the club head passed and display the golf club swing motion. The spatial orientation devices further comprise a digital compass for directional data and accelerometer for spatial static and or spatial translational acceleration data housed inside or mounted to the golf club, game apparatus, sports implement, or gaming device.

Wireless Signal Receiver and Computer

Figure 10:
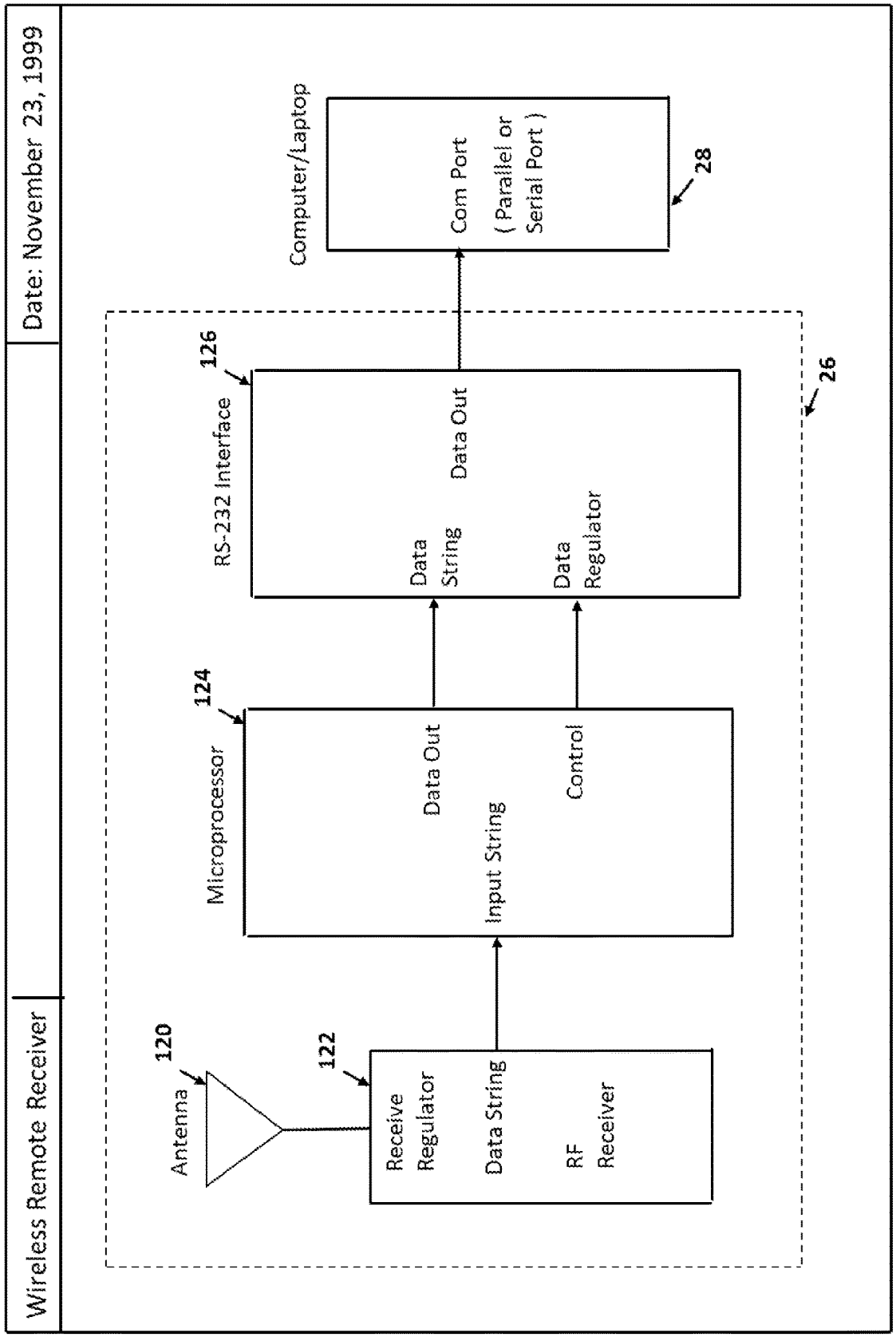
FIG. 10 is a block diagram of a computer installation for use as the computer and information receiving interconnect of the system of FIG. 1.

At each player site, a wireless radio frequency signal receiver 26 is connected to the computer 28 by either the serial (USB) or parallel computer portsT as shown in the functional block diagram, FIG. 10. The wireless signal receiver 26 detects digitally coded radio frequency transmissions from the communication circuit associated with any of a smart golf club 20, a golf ball receptacle 22, or a golf club motion sensing plate 24, as shown in FIG. 1. The received transmissions are demodulated by the RF receiver circuitry 122 (FIG. 10) connected to a processor 124, which converts the demodulated data signal to serial binary coded data suitable for communications to a computer 28. The computer 28, under the control of the internally installed golf system software program, monitors and directs the flow of communications between remotely located players via the internet and displays the game event simulations and performance information. In appropriate installations the wireless electromagnetic signals (e.g., infrared transmitters) that communicate with the receiver may be infrared communications.

Computer Golfing Software

Figure 11:
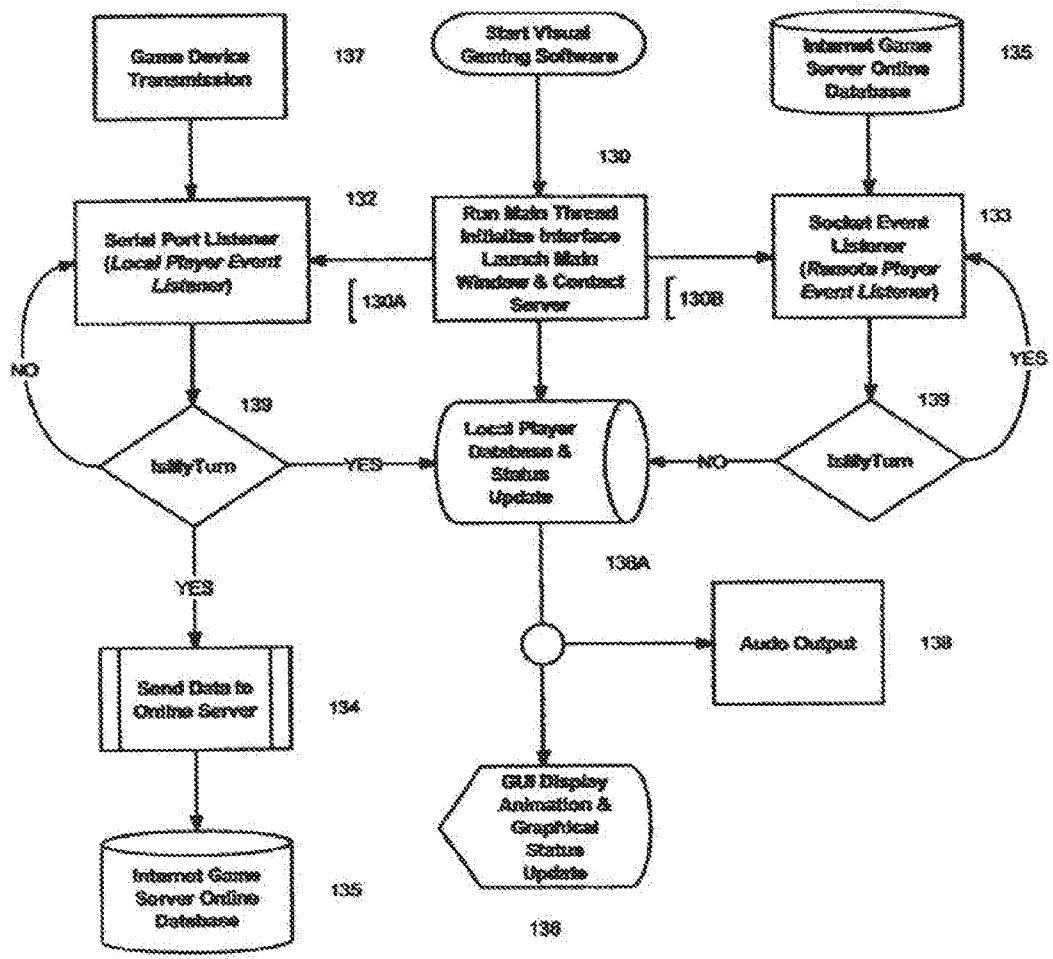
FIG. 11 is a functional block diagram of the software operation of the computer of FIG. 10.

At each remote player site, the computer 28 (FIG. 1) under the control of the golfing software program (shown in the golfing software system functional block diagram, FIG. 11) monitors and controls initialization and the sequential play of the golf game, or alternatively, the individual player practice session. Upon startup by a player at a particular site, the system input parameters are set and the system internet and player port interfaces are initialized 130 as indicated by the arrows 130a and 130b. For internet communications, the serial port listener of the computer 28 is enabled in the preferred embodiment. A remote player event listener is initialized. It will communicate events from one or more of the smart golf club, the golf ball receptacle, and the motion sensor plate. The main operational software (program) thread is run 130, and the system awaits data input from the appropriate computer communications ports at 132 (port), 133 (Remote player Socket Event Listener).

If the competitive play mode has been selected, the program generates a player participation request and sends 134 the request to the GGC game internet server (game server) 34 (FIG. 1).

Figure 12:
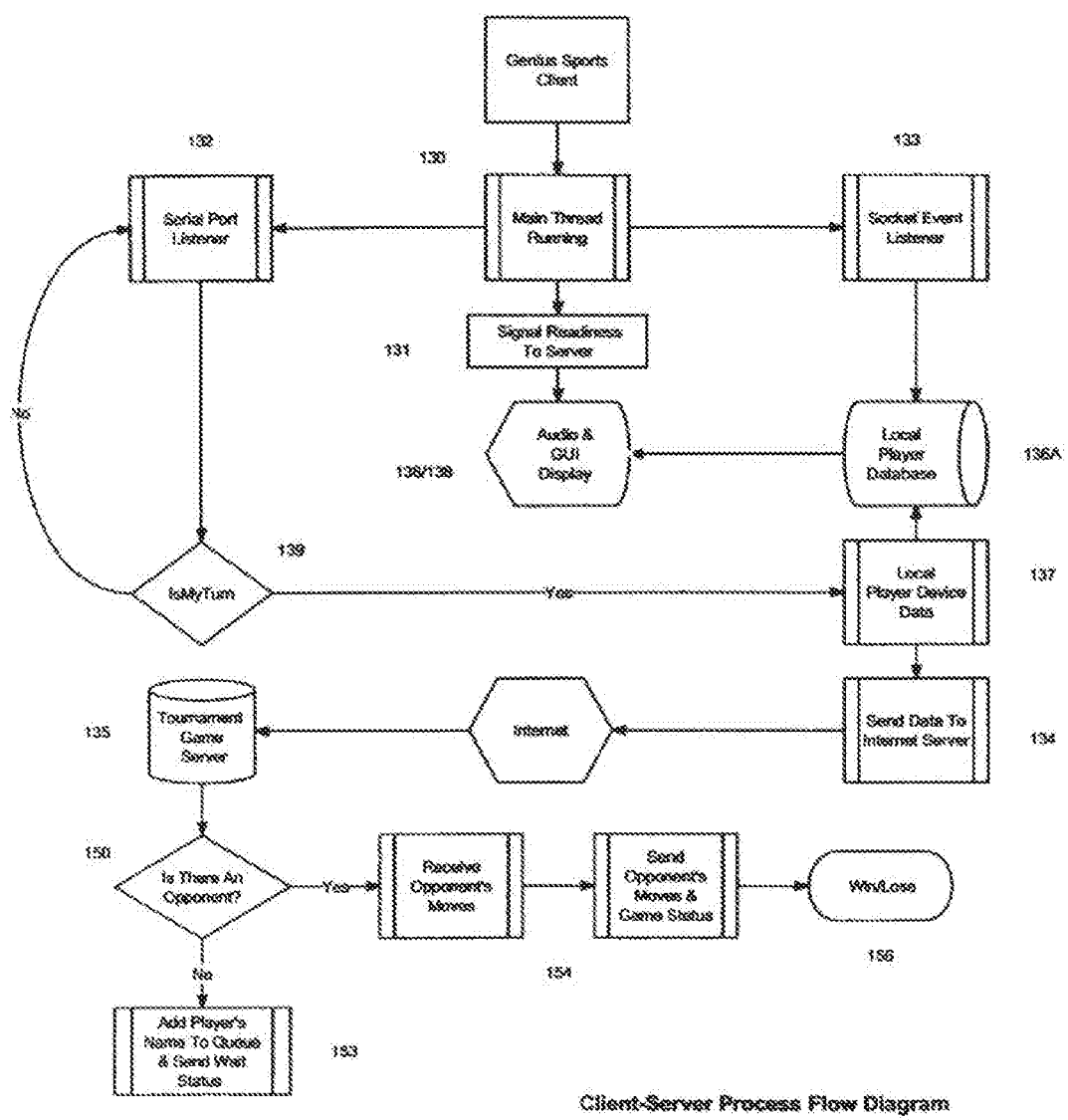
FIG. 12 is a flowchart illustrative of a portion of the operation of the computer of FIG. 10 operating as indicated in the block diagram of FIG. 11.

Upon identification of a player opponent at 150 (FIG. 12) by the game server, the program initiates the player identification sequence 152 and sequential play begins 154 and this software sequence and control routine occurs at each remote site where play has been initiated. During the game play sequences 154, the program generates the appropriate animation, display, and audio data and commands 136 and 138 (FIG. 11), and communicates with the associated display and speaker devices 30 and 31 (FIG. 1). Upon the occurrence of a local computer player event detected at 133, the main operating program at 130, displays the event at 136, and communicates the event at 132 by causing a device transmission at 137 to be sent at 134 via the internet game server 135 which displays the event for the opposing player and alerts the opposing player it is his/her turn to play.

The local computer player event may be, but is not limited to, the smart golf club impacting a ball or projectile, the swing of a club across the sensing plate or the balls entry into the receptacle. The program contains time delay limits for the player action, and delays of play beyond these limits generate play quit and disconnect signals.

The event at 133 also has the effect of indicating at 139 that it is no longer the local computer player's turn and enables (as indicated by line 139) the serial port listener at 132 to detect an event from the remote player, again via the internet.

If the single player practice mode is selected, the internet communications sequences are disabled, other software sequential operating routines continue as above described and the player's golf club stroke, ball-receptacle contact, and/or club swing motion sensor information, are communicated only to the computer located at the player's site and the performance information analyzed and displayed only at the local computer player's site.

When a game is won, lost, or terminated, the golf software system generates the appropriate output signals 156 (FIG. 12), displays the player performance information, and resets to initial pre-game conditions. If one player opponent quits the game or is "timed out" (due to excessive delay in play) and the remaining player wishes to continue play, the software resumes an internet search for another opponent 152 and 153.

Using programming as contained in the accompanying microfiche appendix, one skilled in the art can readily accomplish the game programming described. Alternative programming too will be apparent from the foregoing functional description and the illustrations contained in the appended drawings While, a preferred embodiment has been described, it will be appreciated that many variations and modifications in the system, its operation, and its various components may be made without departure from the spirit and scope of this invention as set forth in the appended claims.

The invention claimed is:

1. A system comprising first and second processors, a first remote computer, a game server, a display screen, a sensor, wireless communication circuitry, and a game apparatus, wherein said first processor is part of an internal electronics circuitry within said game apparatus and said internal electronics circuitry includes a transmitter, one or more sensors, and processing circuit, said first processor further including pre-programmed identification information corresponding to said game apparatus, the sensor disposed on the game apparatus and configured to output sensor data, the first processor receiving data derived from the sensor, the second processor wirelessly coupled to the first processor via the wireless communication circuit, the game apparatus configured to be used in a first game event, the first remote computer being communicatively coupled to the game server via the Internet, operatively coupled to the display screen, and programmed to receive the data derived from the sensor data from the first processor and the second processor, create first visual data using the data received from the second processor to control the display screen and display the first visual data on the display screen in a first three-dimensional animation of the first game event that produced the sensor data, and send the first visual data to the game server via the Internet.

2. The system in claim 1, the first visual data including a simulation of the first game event.

3. The system in claim 1, the sensor configured to be impacted by a game projectile.

4. The system in claim 1, the sensor comprising a motion detector.

5. The system in claim 1, the first processor additionally programmed to determine if impact occurs between a game projectile and the game apparatus based on the sensor data.

6. The system in claim 5, the game apparatus having a hitting surface, the sensor comprising an array of sensors, each sensor of the array of sensors attached to the hitting surface, the sensor configured to derive direction data based on stimulation to the sensors and transmit the direction data to the first processor, the direction data relating to an angle of impact between the game projectile and the game apparatus.

7. The system in claim 5, the sensor comprising an accelerometer, the sensor configured to derive motion data based on stimulation to the accelerometer and transmit the motion data to the first processor, the motion data relating to a three-dimensional acceleration and orientation of the game apparatus.

8. The system in claim 5, the sensor configured to transmit force and time data indicative of a force of the impact between the game projectile and the game apparatus and a time and duration of the force applied.

9. The system in claim 1, the sensor data transmitted by the sensor and received by the first processor from the sensor using a wireless radio frequency protocol.

10. The system in claim 1, wherein the remote computer is communicatively coupled to the second processor via a serial port listener.

11. The system in claim 1, wherein the remote computer is communicatively coupled to the Internet via a socket event listener.

12. The system in claim 1, wherein the first remote computer is further programmed to receive data from the game server via the Internet and create second visual data using the data received from the game server to control the display screen to display the second visual data on the display screen in a second three-dimensional animation of a second game event.

13. The system in claim 12, further comprising a second remote computer communicatively coupled to the game server via the Internet and programmed to create the second visual data based on sensor data produced during a second game event and send the second visual data to the first remote computer via the game server for display on the display screen, wherein the first game event is a first act performed by a first player at a first remote site associated with the first remote computer and the second game event is a second act performed by a second player at a second remote site associated with the second remote computer.

* * * * *